(12) United States Patent
Webb et al.

(10) Patent No.: US 6,652,864 B1
(45) Date of Patent: Nov. 25, 2003

(54) COMPOUNDS FOR INTRACELLULAR DELIVERY OF THERAPEUTIC MOIETIES TO NERVE CELLS

(75) Inventors: Robert R. Webb, Moss Beach, CA (US); Constance A. McKee, Woodside, CA (US)

(73) Assignee: Asilomar Pharmaceuticals, Inc., Woodside, CA (US)

( * ) Notice: Subject to any disclaimer, the term of this patent is extended or adjusted under 35 U.S.C. 154(b) by 0 days.

(21) Appl. No.: 09/217,037

(22) Filed: Dec. 21, 1998

(51) Int. Cl.$^7$ ........................ A61K 38/18; A61K 39/385
(52) U.S. Cl. ................. 424/193.1; 424/194.1; 424/195.11
(58) Field of Search ................. 530/300, 350; 424/178.1, 184.1, 85.1, 193.1, 194.1, 195.11; 514/2–21, 44

(56) References Cited

U.S. PATENT DOCUMENTS

| | | | |
|---|---|---|---|
| 5,389,623 A | 2/1995 | Bodor | |
| 5,502,037 A | 3/1996 | Kondratyev | |
| 5,505,931 A | 4/1996 | Pribish | |
| 5,554,498 A | 9/1996 | Filler et al. | |
| 5,563,250 A | 10/1996 | Hylarides et al. | |
| 5,614,652 A | 3/1997 | Filler et al. | |
| 5,767,288 A | 6/1998 | Rock et al. | |
| 5,833,988 A | 6/1998 | Rock et al. | |
| 5,948,384 A | 9/1999 | Filler | |

FOREIGN PATENT DOCUMENTS

| | | | |
|---|---|---|---|
| WO | WO 95/07092 | | 3/1995 |
| WO | WO 95/32738 | | 12/1995 |
| WO | WO 97/21732 | * | 6/1997 |
| WO | WO 97/23608 | | 7/1997 |
| WO | WO 97/26275 | * | 7/1997 |
| WO | WO9737966 | | 10/1997 |
| WO | WO 00/37103 | | 6/2000 |
| WO | WO 01/91798 A2 | | 6/2001 |

OTHER PUBLICATIONS

Ponzetto et al., Hepatology, 14:16–24, 1991.*
Fiume et al., Biochem. Pharmacol. 35:967–72, 1986.*
Wilcox et al., J. of Virology Feb. 62(2):393–99, 1988.*
Fiume et al., FEBS 3810, 203(2):203–206, 1986.*
Skolnick et al., Trends in Biotech., 18(1):34–39, 2000.*
Choh et al., PNAS 77(6):3211–14, 1980.*
Haschke et al., J. of Neurochem., 1980 Dec., 35(6):1431–5.*
Kramer et al., "Monoclonal Antibody to Human Trk–A; Diagnostic and Therapeutic Potential in Neuroblastoma," *European Journal of Cancer* vol. 33 No. 12: pp. 2092–2091 (Oct. 1997).*
Pardridge et al., "Transport of Human Recombinant Brain–Derived Neurotarophic Factor (BDNF) Through the Rat Blood–Barin Barrier in Vivo Using Vector–Mediated Peptide Drug Delivery," *Pharmaceutical Research* vol. 11, No. 5: pp. 738–746 (1994).*
Schwab, M.E., "Ultrastructural localization of a nerve growth factor–horseadish peroxidase (NGF–HRP) coupling product after retrogade axonal transport in adrenergic neurons", *Brain Research*, vol. 130, No. 1, Jul. 8, 1977, pp. 190–196.
Schwab, M.E. et al., "Labeled wheat germ agglutinin (WGA) as a new, highly sensitive retrograde tracer in the rat brain hippocampal system", *Brain Research*, vol. 152, No. 1, Aug. 18, 1978, pp. 145–150.
Schwab, M.E. et al., "Selective Retrograde Transsynaptic Transfer of a Protein, Tetanus Toxin, Subsequent to Its Retrograde Axonal Transport", *J. Cell Biology*, vol. 82, No. 3, Sep. 1979, pp. 798–810.
Maliartchouk, S. et al., "Optimal Nerve Growth Factor Trophic Signals Mediated by Synergy of TrkA and p75 Receptor–Specific Ligands", *The Journal of Neuroscience*, vol. 17, No. 16, Aug. 1997, pp. 6031–6037.
Binkley, J. et al., "RNA ligands to human nerve growth factor", *Nucleic Acids Research*, vol. 23, No. 16 (1995), pp. 3198–3205.

* cited by examiner

*Primary Examiner*—Gary Kunz
*Assistant Examiner*—Stephen Gucker
(74) *Attorney, Agent, or Firm*—Carol L. Francis; Bozicevic, Field & Francis LLP

(57) ABSTRACT

A compound for delivering a non-cytotoxic therapeutic moiety into nerve cells, the compound having the general formula:

B—L—TM where:
B is a binding agent capable of selectively binding to a nerve cell surface receptor and mediating absorption of the compound by the nerve cell;
TM is a therapeutic moiety which has a non-cytotoxic therapeutic effect when absorbed by a nerve cell; and
L is a linker coupling B to TM.

16 Claims, No Drawings

COMPOUNDS FOR INTRACELLULAR DELIVERY OF THERAPEUTIC MOIETIES TO NERVE CELLS

FIELD OF THE INVENTION

The present invention relates to compounds which can be used to selectively deliver moieties to nerve cells. More specifically, the invention relates to compounds which include a therapeutic moiety and facilitate absorption of the therapeutic moiety by nerve cells.

BACKGROUND OF THE INVENTION

Our understanding of the structure and function of the nervous system has been greatly advanced owing to enormous progresses made in field of neuroscience. Cellular and molecular mechanisms of neuron growth and development and diseases associated with the central and peripheral nervous systems are studied extensively by using rapidly growing techniques in molecular and cell biology. However, a need still exists for efficacious treatments of many neurological disorders including Alzheimer's disease, Parkinson's disease, Huntington's disease, schizophrenia, severe pain, multiple sclerosis, bipolar disease, and diseases of the nervous system due to infection by viruses and other microorganisms (herpes simplex, HIV, cytomegalovirus, parasites, fungi, prion, etc.).

Many neuropharmaceutical agents have been developed to treat diseases of the nervous system, but their usefulness has been hampered by severe side effects partially due to nonspecific interactions between these agents and cells or tissues other than the targeted cells. For example, steroid hormone cortisone and its derivatives are widely used to treat inflammation in the body including the nerve system to reduce symptoms such as swelling, tenderness and pain. However, the steroid dosage has to be kept at the lowest effective level because of its severe side effects. Steroid hormone binds to its cognate nuclear hormone receptor and induces a cascade of cellular effects, including programmed cell death of the neurons in the brain (Kawata M., et al., J. Steroid Biochem. Mol. Biol. 65: 273–280 (1998)). Since steroid hormone receptors, such as glucocorticord receptor for cortisone, distribute in a wide variety of tissues and cells, nonspecific interactions of the hormone with its cognate receptor in different sites is unavoidable if the drug is circulated systemically.

A need continues to exist for an effective system for delivering therapeutic agents selectively to nerve cells and nerve tissues. Various techniques have been developed to deliver drugs, but with only limited success. For example, liposomes have been used as carrier molecules to deliver a broad spectrum of agents including small molecules, DNAs, RNAs, and proteins. Liposome mediated delivery of pharmaceutical agents has major drawbacks because of its lack of target specificity. Attempts have been made to overcome this problem by covalently attaching whole site-specific antibody or Fab fragments to liposomes containing a pharmaceutical agent (Martin et al., Biochem. 20, 4229–4238, (1981)). However, an intrinsic problem of particular importance in any liposome carrier system is that in most cases the targeted liposome does not selectively reach its target site in vivo. Whether or not liposomes are coated with antibody molecules, liposomes are readily phagocytosed by macrophages and removed from circulation before reaching their target sites.

SUMMARY OF THE INVENTION

Compounds of the present invention include compounds having the general formula:

B—L—M where:
B is a binding agent capable of selectively binding to a nerve cell surface receptor and mediating absorption of the compound by the nerve cell;
M is a moiety which performs a useful non-cytotoxic function when absorbed by a nerve cell; and
L is a linker coupling B to M.

In one embodiment, the compounds have the general formula:

B—L—TM where:
B is a binding agent capable of selectively binding to a nerve cell surface receptor and mediating absorption of the compound by the nerve cell;
TM is a therapeutic moiety which has a non-cytotoxic therapeutic effect when absorbed by a nerve cell; and
L is a linker coupling B to TM.

In another embodiment, the compounds have the general formula:

B—L—IM where:
B is a binding agent capable of selectively binding to a nerve cell surface receptor and mediating absorption of the compound by the nerve cell;
IM is a non-cytotoxic imaging moiety which can be used to image a nerve cell or an intracellular component of the nerve cell; and
L is a linker coupling B to IM.

In regard to each of the above embodiments, particular classes of binding agents B which may be used include, but are not limited to, nucleic acid sequences, peptides, peptidomimetics, antibodies and antibody fragments. Examples of nucleic acids that can serve as the binding agent B include, but are not limited to, DNA and RNA ligands that function as antagonists of nerve growth factors or inhibit binding of other growth factors to nerve cell surface receptors. Examples of peptides that can serve as the binding agent B include, but are not limited to, members of the nerve growth factors (neurotrophin) family such as NGF, BDNF, NT-3, NT-4, NT-6; derivatives, analogs, and fragments of nerve growth factors such as recombinant molecules of NGF and BDNF; and synthetic peptides that bind to nerve cell surface receptors and have agonist or antagonist activities of nerve growth factors.

Antibodies, derivatives of antibodies and antibody fragments can also serve as the binding agent B. Examples of this type of binding agent B include, but are not limited to, anti-human trka monoclonal antibody 5C3 and anti-human p75 monoclonal antibody MC192.

The therapeutic moiety TM is selected to perform a non-cytotoxic therapeutic function within nerve cells. Examples of non-cytotoxic functions which the therapeutic moiety TM may perform include, but are not limited to, the functions performed by adrenergic agents, analgesics, anti-trauma agents, anti-viral agents, gene therapy agents, and hormones (growth factors, interferons, etc.). Examples of classes of therapeutic moieties include, but are not limited to, adrenergic agents (e.g., epinephrine, norepinephrine, dopamine, etenolol), analgesics (e.g., opioids, codeine, oxycodone), anti-trauma agents, anti-viral agents (e.g., acyclovir, gancyclovir, AZT, ddI, ddC, etc.), gene therapy agents (e.g., DNAs or RNAs which introduce a gene or replace a mutated gene), steroids (e.g., cortisone, progesterone, estrogen), and hormones (e.g., growth factors, interferons).

The imaging moiety IM is a non-cytotoxic agent which can be used to locate and optionally visualize a nerve cell or an internal component of the nerve cell which has absorbed the imaging moiety. Fluorescent dyes may be used as an imaging moiety IM. Radioactive agents which are non-cytotoxic may also be an imaging moiety IM.

In general, the linker may be any moiety which can be used to link the binding agent B to the moiety M. In one particular embodiment, the linker is a cleavable linker. The use of a cleavable linker enables the moiety M linked to the binding agent B to be released from the compound once absorbed by the nerve cell. The cleavable linker may be cleaved by a chemical agent, enzymatically, due to a pH change, or by being exposed to energy. Examples of forms of energy which may be used include light, microwave, ultrasound, and radiofrequency.

The present invention also relates to a method for selectively delivering a moiety into nerve cells comprising the steps of:

delivering to a patient a compound having the general formula:

B—L—M where:

B is a binding agent capable of selectively binding to a nerve cell surface receptor and mediating absorption of the compound by the nerve cell;

M is a moiety which performs a useful non-cytotoxic function when absorbed by a nerve cell; and L is a linker coupling B to M.

having the compound selectively bind to a nerve cell surface receptor via the binding agent B; and having the compound be absorbed by the nerve cell mediated by the binding of the binding agent B to the nerve cell surface receptor.

In one embodiment, moiety M is a therapeutic moiety TM as described herein and in another embodiment is an imaging moiety IM.

The above method can be used to deliver therapeutic moieties for treating a variety of neurological disorders when the therapeutic moiety TM is a moiety useful for treating such neurological disorders.

The above method can be used to deliver therapeutic moieties for treating pain when a therapeutic moiety TM for treating pain, such as an analgesic, is included as the therapeutic moiety TM in the compound.

The above method can also be used to deliver steroid hormones for treating nerve damage when a therapeutic moiety TM for treating nerve damage, such as a steroid hormone, is included as the therapeutic moiety TM in the compound.

The above method can also be used to stimulate nerve growth when a therapeutic moiety TM for inducing the production of a nerve growth factor is included as the therapeutic moiety TM in the compound.

The above method can also be used to treat infected nerve cells infected with viruses or immunize nerve cells from viruses when the therapeutic moiety TM in the compound is an antiviral agent.

The above method can also be used to perform gene thereapy when the therapeutic moiety TM is a gene therapy agent.

DETAILED DESCRIPTION

The present invention relates to compounds which include a binding agent which binds to a nerve cell surface receptor and facilitates absorption of the compound by the nerve cell; and a moiety. Different Moieties may be included in the compounds of the present invention including therapeutic moieties that are non-cytotoxic to the nerve cells and imaging moieties which can be used to image nerve cells which absorb these compounds.

In one embodiment, compounds of the present invention have the general formula:

B—L—TM where:

B is a binding agent capable of selectively binding to a nerve cell surface receptor and mediating absorption of the compound by the nerve cell;

TM is a therapeutic moiety which has a non-cytotoxic therapeutic effect when absorbed by a nerve cell; and L is a linker coupling B to TM.

According to this embodiment, the binding agent B serves as a homing agent for nerve cells by selectively binding to nerve cell surface receptors. The binding agent B also serves to facilitate absorption of the compound by the nerve cell. The binding agent B can be any molecule which can perform these two functions. Particular classes of binding agents which may be used include, but are not limited to, nucleic acid sequences, peptides, peptidomimetics, antibodies and antibody fragments.

Examples of nucleic acids that can serve as the binding agent B include, but are not limited to, DNA and RNA ligands that function as antagonists of nerve growth factors or inhibit binding of other growth factors to nerve cell surface receptors (Binkley, J., et al., Nucleic Acid Res. 23: 3198–3205 (1995); Jellinek, D., et al., Biochem. 33:10450–10456 (1994)).

Examples of peptides that can serve as the binding agent B include, but are not limited to, members of the nerve growth factors (neurotrophin) family such as NGF, BDNF, NT-3, NT4, NT-6, etc. (see reviews: Frade, J. M., et al., Bioessays 20: 137–145 (1998); Shieh, P. B., Curr. Biol. 7: R627–R630 (1997); Dechant, G., et al., Curr. Opin. Neurobiol. 7: 413–418 (1997); Chao, M. V. and Hempstead, B. L., Trends Neurobiol. 18: 321–326 (1995)); and derivatives, analogs, and fragments of nerve growth factors such as recombinant molecules of NGF and BDNF (Ibanez et al., EMBO J. 10: 2105–2110; Ibanez et al., EMBO J. 12: 2281–2293), synthetic peptides that bind to nerve cell surface receptors and have agonist or antagonist activities of nerve growth factors (Longo, F. M., et al., Cell Regulation 1: 189–195 (1990); LeSauteur, L. et al., J. Biol. Chem. 270: 6564–6569 (1995); Longo F. M., et al., J. Neurosci. Res. 48: 1–17; Longo, et al., Nature Biotech. 14: 1120–1122 (1997)).

Examples of antibodies, derivatives of antibodies and antibody fragments that can serve as the binding agent B include, but are not limited to, anti-human trka monoclonal antibody 5C3 (Kramer, K., et al., Eur. J. Cancer 33: 2020–2091 (1997)), anti-human p75 monoclonal antibody MC192 (Maliatchouk, S. and Saragovi, H. U., J. Neurosci. 17: 6031–7).

According to this embodiment, the therapeutic moiety TM is selected to perform a non-cytotoxic therapeutic function within nerve cells. Examples of non-cytotoxic functions which the therapeutic moiety TM may perform include, but are not limited to, the functions performed by analgesics, anti-trauma agents, anti-viral agents, gene therapy agents, and hormones (growth factors, interferons, etc.). Examples of classes of therapeutic moieties include, but are not limited to, adrenergic agents (e.g., epinephrine, norepinephrine, dopamine, etenolol), analgesics (e.g., opioids, codeine, oxycodone), anti-trauma agents, anti-viral agents (e.g., acyclovir, gancyclovir, AZT, ddI, ddC, etc.), gene therapy agents (e.g., DNAs or RNAs which introduce a gene or replace a mutated gene), steroids (e.g., cortisone, progesterone, estrogen), and hormones (e.g., growth factors, interferons).

The linker L serves to link the binding agent B to the therapeutic moiety TM. A wide variety of linkers are known in the art for linking two molecules together, particularly for linking a moiety to a peptide or nucleic acid, all of which are included within the scope of the present invention.

Examples of classes of linkers that may be used to link the binding agent B to the therapeutic moiety TM include amide, alkylamine, thiolether, alkyl, cycloalkyl, aryl linkages such as those described in Hermanson, G. T., Bioconjugate Techniques (1996), Academic Press, San Diego, Calif.

In certain applications, it is desirable to release the therapeutic moiety TM once the compound has entered the nerve cell, resulting in a release of the therapeutic moiety TM. Accordingly, in one variation, the linker L is a cleavable linker. This enables the therapeutic moiety TM to be released from the compound once absorbed by the nerve cell. This may be desirable when the therapeutic moiety TM has a greater therapeutic effect when separated from the binding agent. The therapeutic moiety TM may have a better ability to be absorbed by an intracellular component of the nerve cell when separated from the binding agent. Accordingly, it may be necessary or desirable to separate the therapeutic moiety TM from the compound so that the therapeutic moiety TM can enter the intracellular compartment.

Cleavage of the linker releasing the therapeutic moiety may be as a result of a change in conditions within the nerve cells as compared to outside the nerve cells, for example, due to a change in pH within the nerve cell. Cleavage of the linker may occur due to the presence of an enzyme within the nerve cell which cleaves the linker once the compound enters the nerve cell. Alternatively, cleavage of the linker may occur in response to energy or a chemical being applied to the nerve cell. Examples of types of energies that may be used to effect cleavage of the linker include, but are not limited to light, ultrasound, microwave and radiofrequency energy.

The linker L used to link the binding agent B to the therapeutic moiety TM may be a photolabile linker. Examples of photolabile linkers include those linkers described in U.S. Pat. Nos. 5,767,288 and 4,469,774. The linker L used to link the binding agent B to the therapeutic moiety TM may also be an acid labile linker. Examples of acid labile linkers include linkers formed by using cis-aconitic acid, cis-carboxylic alkatriene, polymaleic anhydride, and other acidlabile linkers, such as those linkers described in U.S. Pat. Nos. 5,563,250 and 5,505,931.

Further examples of cleavable linkers include, but are not limited to the linkers described in Lin, et al., J. Org. Chem. 56:6850–6856 (1991); Ph.D. Thesis of W.-C. Lin, U. C. Riverside, (1990); Hobart, et al., J. Immunological Methods 153: 93–98 (1992); Jayabaskaran, et al., Preparative Biochemistry 17(2): 121–141 (1987); Mouton, et al., Archives of Biochemistry and Biophysics 218: 101–108 (1982); Funkakoshi, et al., J. of Chromatography 638:21–27 (1993); Gildea, et al., Tetrahedron Letters 31: 7095–7098 (1990); WO 85/04674; and Dynabeads (Dynal, Inc., 5 Delaware Drive, Lake Success, N.Y. 11042).

In another embodiment, compounds of the present invention have the general formula:

B—L—IM where:
B is a binding agent capable of selectively binding to a nerve cell surface receptor and mediating absorption of the compound by the nerve cell;
IM is a non-cytotoxic imaging moiety which can be used to image the nerve cell or an intracellular component of the nerve cell; and
L is a linker coupling B to IM.

According to this embodiment, the binding agent B and linker L may be varied as described above with regard to compounds having the general formula B—L—TM. Further according to this embodiment, the imaging moiety IM may be a non-cytotoxic moiety which can be used to image nerve cells. Examples of imaging moieties that may be used include fluorescent dyes and radioisotopes which are non-cytotoxic.

The present invention also relates to a method for selectively delivering a non-cytotoxic therapeutic moiety into nerve cells comprising the steps of:
delivering to a patient a therapeutic amount of a compound having the general formula:

B—L—TM where:
B is a binding agent capable of selectively binding to a nerve cell surface receptor and mediating absorption of the compound by the nerve cell,
TM is a therapeutic moiety which has a non-cytotoxic therapeutic effect when absorbed by a nerve cell, and
L is a linker coupling B to TM;
having the compound selectively bind to a nerve cell surface receptor via the binding agent B; and
having the compound be absorbed by the nerve cell mediated by the binding of the binding agent B to the nerve cell surface receptor.

The method of the present invention offers the advantage of specifically targeting a non-cytotoxic therapeutic moiety to nerve cells where the therapeutic moiety is absorbed by the nerve cells. The method utilizes the fact that internalization of the conjugated agent is mediated by the binding of the binding agent B to nerve cell surface receptors. Once internalized, the therapeutic moiety can accumulate within the nerve cells where it has a therapeutic effect. The ability to selectively deliver the compound to nerve cells reduces the overall amount of therapeutic moiety which needs to be administered. Selective delivery of the therapeutic moiety to the nerve cell reduces the amount of side effects observed due to non-specific administration of the therapeutic moiety. In addition, the therapeutic moiety is less likely to be separated from the binding agent and non-specifically administered as compared to delivery methods involving the use of a binding agent and a therapeutic moiety in combination.

The method of the present invention can be used to deliver therapeutic moieties for treating a variety of neurological disorders including, but not limited to, Alzheimer's disease, Parkinson's disease, multiple sclerosis, neurodegenerative disease, epilepsy, seizure, migraine, trauma and pain. Examples of neuropharmaceuticals that may be used include proteins, antibiotics, adrenergic agents, anticonvulsants, nucleotide analogs, anti-trauma agents, peptides and other classes of agents used to treat or prevent a neurological disorders. For example, analgesics such as opioids, codeine and oxycodone can be conjugated to the binding agent B and specifically delivered to the nerve cells. Since the same level of pain relief can be achieved using a smaller dosage of analgesics, side effects such as respiratory depression or potential drug addiction can be avoided or at least ameliorated. Steroid hormones such as corticosteriods can also be conjugated with nerve cell-specific binding agents and used to treat inflammation of the nerves, which may reduce the side effects associated with high doses of steroids, such as weight gain, redistribution of fat, increase in susceptibility to infection, and avascular necrosis of bone.

The method according to the present invention can also be used to deliver agents that induce the production of nerve growth factor in the target nerve cells, especially under conditions of pathogenic under-expression of NGFs (See Riaz, S. S. and Tomlinson, D. R. Prog. Neurobiol. 49: 125–143 (1996)). NGF induction has been demonstrated in a wide variety of cell types, such as fibroblasts (Furukawa, Y. et al., FEBS Lett. 247: 463–467(1989)), astrocytes (Furukawa, Y. et al., FEBS Lett. 208: 258–262 (1986)), Schwann cells (Ohi, T. et al., Biochem. Int. 20:739–746 (1990)) with a variety of agents including cytokines, steriods, vitamins, hormones, and unidentified components of serum. Specific examples of agents known to induce NGF include 4-methylcatechol, clenbuterol, isoprenaline, L-tryptophan, 1,25-dihydroxyvitamin D3, forskolin, fellutamide A, gangliosides and quinone derivatives (Riaz, S. S. and Tomlinson, D. R. Prog. Neurobiol. 49: 125–143 (1996)).

The method according to the present invention can also be used to deliver antiviral drugs into nerve cells in order to treat diseases caused by viral infection, to eliminate viruses spread to the nerves, and to inhibit infection by such viruses. Examples of viruses that infect the nervous system include but are not limited to rabies viruses, herpes viruses, polioviruses, arboviruses, reoviruses, pseudorabies, corona viruses, and Borna disease viruses. For example, antiviral drugs such as acyclovir, gancyclovir, and Cifodovir can be conjugated to the binding agent and used to inhibit active or latent herpes simplex viruses in the peripheral and central nervous system. Specific delivery of the conjugate containing these antiviral drugs to the nervous system can reduce the side effects associated with high doses or long-term administration of these drugs, such as headaches, rash and paresthesia.

The method according to the present invention can also be used to deliver marker compounds to image intracellular components of the nerve cells. Such marker compounds include but are not limited to fluorescent dyes, radioactive complexes, and other luminophores.

The method according to the present invention can also be used to perform gene therapy wherein nucleic acids (DNA or RNA) are delivered to the nerve cells. These nucleic acids may serve to replace genes which are either defective, absent or otherwise not properly expressed by the patient's nerve cell genome.

The above and other features and advantages of the present invention will become more apparent in the following description of the preferred embodiments in greater detail.

1. Binding Agent (B)

According to the present invention, a compound with a binding agent B is used to selectively deliver the conjugated therapeutic moieties TM to nerve cells. At the nerve cell, the binding agent B interacts with a receptor on the nerve cell and is absorbed by the nerve cell mediated by this interaction. Any molecules possessing these two physical properties are intended to fall within the scope of a binding agent B as it is used in the present invention. In particular, peptides or proteins with these features can serve as a binding agent B, examples including but not limited to nerve growth factors (neurotrophins), antibodies against nerve cell-specific surface proteins, mutants and synthetic peptides derived from these peptides or proteins.

In one embodiment, neurotrophins are preferably used as the binding agent B. Neurotrophins are a family of small, basic polypeptides that are required for the growth, development and survival of neurons. A particular "survival" factor is taken up by the neuron via binding to one or more of a related family of transmembrane receptors. Table 1 lists several members of the neurotrophin family and their cognate receptors.

As listed in Table 1, nerve growth factor (NGF) is the first identified and probably the best characterized member of the neurotrophin family. It has prominent effects on developing sensory and sympathetic neurons of the peripheral nervous system. Brain-derived neurotrophic factor (BDNF) has neurotrophic activities similar to NGF, and is expressed mainly in the CNS and has been detected in the heart, lung, skeletal muscle and sciatic nerve in the periphery (Leibrock, J. et al., Nature, 341:149–152 (1989)). Neurotrophin-3 (NT-3) is the third member of the NGF family and is expressed predominantly in a subset of pyramidal and granular neurons of the hippocampus, and has been detected in the cerebellum, cerebral cortex and peripheral tissues such as liver and skeletal muscles (Ernfors, P. et al., Neuron 1: 983–996 (1990)). Neurotrophin4 (also called NT-4/5) is the most variable member of the neurotrophin family. Neurotrophin-6 (NT-6) was found in teleost fish and binds to p75 receptor.

As listed in Table 1 at least two classes of transmembrane glycoproteins (trk and p75) have been identified which serve as receptors for neurotrophins. The trk receptors (tyrosine kinase-containing receptor) bind to neurotrophins with high affinity, whereas the p75 receptors possess lower affinity to neurotrophins. For example, nerve growth factor (NGF) binds to a relatively small number of trka receptors with high affinity ($K_D=10^{-11}$) and to more abundant p75 with lower affinity ($K_D=10^{-9}$). The receptor-bound NGF is internalized with membrane-bound vesicles and retrogradely transported the neuronal cell body. Thus, native neurotropins may serve as the binding agent B in the compound according the present invention to deliver the conjugated therapeutic agent TM to the neuronal cell body.

TABLE 1

The Neurotrophin Family and Its Receptors.

| | Receptor | | Responsive neurons |
|---|---|---|---|
| Factor | Kinase isoforms | Nonkinase forms | (examples) |
| NGF | trkA | p75 | Cholinergic forebrain neurons<br>Sympathetic ganglia<br>DRG nociceptive |

TABLE 1-continued The Neurotrophin Family and Its Receptors.

| | Receptor | | Responsive neurons |
|---|---|---|---|
| Factor | Kinase isoforms | Nonkinase forms | (examples) |
| BDNF | trkB | $p75^{LNTR}$ | Many CNS populations |
| | | $trkB_{T1}$ | Vestibular ganglia |
| | | $trkB_{T2}$ | Nodose ganglia |
| | | | DRG mechanoreceptors |
| NT-3 | trkC | $p75^{LNTR}$ | Many CNS populations |
| | trkB and trkA | | Choclear ganglia |
| | Nonpreferred | $trkC_{TK-113}$ | DRG proprioceptive |
| | | $trkC_{TK-108}$ | |
| NT-4 | trkB | p75 | Many CNS populations |
| | | $trkB_{T1}$ | Nodose ganglia |
| | | $trkB_{T2}$ | Petrosalganglia |
| NT-6 | trkA | p75 | |

In addition to the neurotrophins described above, analogs and derivatives of neurotrophins may also serve as the binding agent B. The structure of mouse NGF has been solved by X-ray crystallography at 2.3 A resolution (McDonald et al., Nature, 345: 411–414, (1991)). Murine NGF is a dimeric molecule, with 118 amino acids per protomer. The structure of the protomer consists of three antiparallel pairs of beta strands that form a flat surface, four loop regions containing many of the variable residues between different NGF-related molecules, which may determine the different receptor specificities, and a cluster of positively charged side chains, which may provide a complementary interaction with the acidic low-affinity NGF receptor. Murine NGF has a tertiary structure based on a cluster of three cysteine disulfides and two extended, but distorted beta-hairpins. One of these β-hairpin loops was formed by the NGF 29–35 region. Structure/function relationship studies of NGF and NGF-related recombinant molecules demonstrated that mutations in NGF region 25–36, along with other β-hairpin loop and non-loop regions, significantly influenced NGF/NGF-receptor interactions (Ibanez et al., EMBO J., 10, 2105–2110, (1991)). Small peptides derived from this region have been demonstrated to mimic NGF in binding to trkA receptor and affecting biological responses (LeSauteur et al. J. Biol. Chem. 270, 6564–6569, 1995). Dimers of cyclized peptides corresponding to β-loop regions of NGF were found to act as partial NGF agonists in that they had both survival-promoting and NGF-inhibiting activity while monomer and linear peptides were inactive (Longo et al., J. Neurosci. Res., 48, 1–17, 1997). Cyclic peptides have also been designed and synthesized to mimic the β-loop regions of NGF, BDNF, NT3 and NT-4/5. Certain monomers, dimers or polymers of these cyclic peptides may have a three-dimensional structure which binds to neurotrophin receptors under physiological conditions. All of these structural analogs of neurotrophins that bind to nerve cell surface receptors and are internalized can serve as the binding agent B of the compound according to the present invention to deliver the conjugated therapeutic moiety TM to the nervous system.

Alternatively, antibodies against nerve cell surface receptors that are capable of binding to the receptors and being internalized can also serve as the binding agent B. For example, monoclonal antibody (MAb) 5C3 is specific for the NGF docking site of the human p140 trka receptor, with no cross-reactivity with human trkB receptor. MAb 5C3 and its Fab mimic the effects of NGF in vitro, and image human trk-A positive tumors in vivo (Kramer et al., Eur. J. Cancer, 33, 2090–2091, (1997)). Molecular cloning, recombination, mutagenesis and modeling studies of Mab 5C3 variable region indicated that three or less of its complementarity determining regions (CDRS) are relevant for binding to trkA. Assays with recombinant CDRs and CDR-like synthetic polypeptides demonstrated that they had agonistic bioactivities similar to intact Mab 5C3. Monoclonal antibody MC192 against p75 receptor has also been demonstrated to have neurotrophic effects. Therefore, these antibodies and their functionally equivalent fragments can also serve as the binding agent B of the compound according to the present invention to deliver the conjugated therapeutic agent TM into the nerve cells.

Alternatively, peptidomimetics that are synthesized by incorporating unnatural amino acids or other organic molecules may serve as the binding agent B of the compound according to the present invention to deliver the conjugated therapeutic agent TM into the nerve cells. These synthetic peptide mimics are capable of binding to the nerve cell surface receptor and being internalized into the cell.

It is noted that the identification and selection of moieties which can serve as binding agents in the present invention can be readily performed by attaching an imaging moiety IM to the potential binding agent in order to detect whether the potential binding agent is internalized by the nerve cells. In this regard, combinatorial and mutagenesis approaches may be used to identify analogs, derivatives and fragments of known binding moieties which may also be used as binding moieties according to the present invention.

2. Therapeutic Moiety (TM)

An aspect of the present invention relates to the delivery of compounds into nerve cells which are non-cytotoxic to the nerve cells and perform a therapeutic function. Examples of therapeutic functions include, but are not limited to, treatment of neurological disorders, gene therapy, intracellular target imaging, cell sorting, or separation schemes. Examples of classes of therapeutic moieties include, but are not limited to adrenergic agents such as epinephrine, norepinephrine, dopamine, etenolol; analgesics such as opioids, codeine, oxycodone; anti-trauma agents; antiviral agents such as acyclovir, gancyclovir, AZT, ddI, ddC; gene therapy agents such as; steroids such as cortisone, progesterone, estrogen; and hormones such as growth factors and interferons. Such compounds may optionally also include an imaging moiety, such as fluorescent moieties, for imaging intracellular components of the nerve cells.

3. Linker (L)

According to the present invention, a binding agent B is linked to a therapeutic moiety TM by a linker L. In general, any method of linking a binding agent to a therapeutic moiety may be used and is intended to fall within the scope of the present invention.

Many different types of linkers have been developed for cross linking proteins and conjugating proteins or peptides with other agents. These linkers include zero-length cross linkers, homobifunctional cross-linkers, heterobifunctional cross-linkers and trifunctional cross-linkers. These linkers may have different susceptibility to cleavage under certain conditions. Depending on a particular application according to the present invention, an appropriate linker may be chosen. When an intracellular release of the agent from its conjugate is desired, a cleavable linker is chosen which is susceptible to cleavage by external stimuli such as light and heat, by intracellular enzymes, or by a particular microenvironment inside the cell.

In one embodiment, the linker L has one of the following general structures:

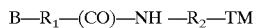

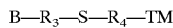

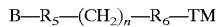

Wherein $R_1$, $R_2$, $R_3$, $R_4$, $R_5$, and $R_6$ are independently selected from the group consisting of alkyls, aryls, heteroaryls, cycloalkyls, cycloalkenes and heterocycloalkenes.

4. Cleavable Linkers

One particular embodiment of the present invention relates to compounds which include a cleavable linker L. In some instances, the therapeutic moiety TM is more efficacious or potent when free from a carrier molecule such as a binding agent. In such instances, it is desirable to utilize a cleavable linker which allows the therapeutic moiety TM to be released from the compound once inside the cell.

Many cleavable linker groups have been developed which are susceptible to cleavage and by a wide variety of mechanisms. For example, linkers have been developed which may be cleaved by reduction of a disulfide bond, by irradiation of a photolabile bond, by hydrolysis of derivatized amino acid side chain, by serum complement-mediated hydrolysis, and by acid-catalyzed hydrolysis.

Examples of photolabile linkers that may be used include those linkers described in U.S. Pat. Nos. 5,767,288 and 4,469,774.

Acid-labile linkers are preferred in the practice of the present invention by taking advantage of a cell's receptor-mediated endocytosis pathways. Receptors that are internalized by receptor-mediated endocytosis pass through acidified compartments known as endosomes or receptosomes. Since the interior of the endosomal compartment is kept acidic (pH~6.0) by ATP-driven $H^+$ pumps in the endosomal membrane that pump $H^+$ into the lumen from the cytosol, a change in pH within the nerve cell can be used to cause the acid-labile linker to be cleaved and release the therapeutic moiety. Examples of acid labile linkers which may be used include the cis-aconitic acid, cis-carboxylic alkatriene, polymaleic anhydride, and other acid labile linkers described in U.S. Pat. Nos. 5,563,250 and 5,505, 931.

5. Examples Of Compounds According To The Present Invention

Table 2 provides several compounds according to the present invention. It is noted that in each instance, the particular therapeutic moieties, binding moieties, and linkers shown may be interchanged with other suitable therapeutic moieties, binding moieties, and linkers. In this regard, the compounds shown in the table are intended to illustrate the diversity of compounds provided according to the present invention.

TABLE 2

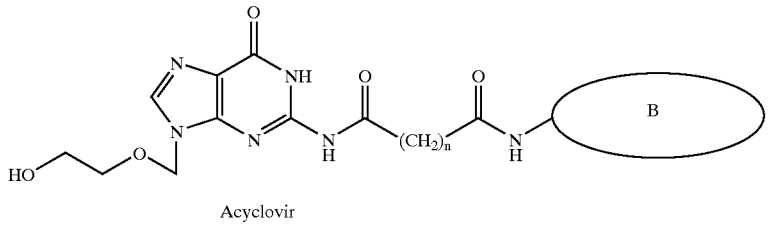

Acyclovir wherein B is selected from the group consisting of nerve growth factors NGF, BDNF, NT-3, NT-4, NT-6, anti-neurotrophin receptor antibodies MAb 5C3 and Mab MC192.

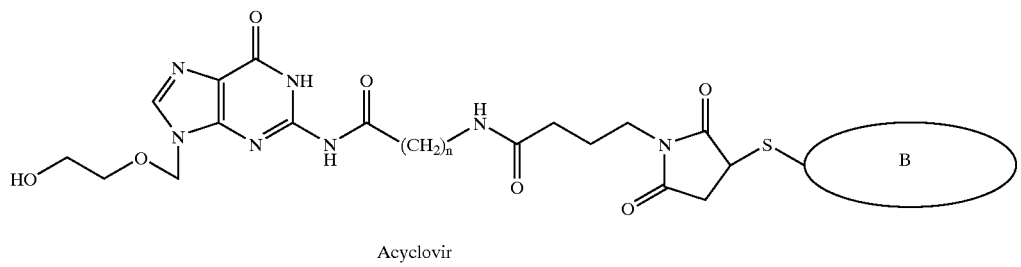

Acyclovir wherein B is selected from the group consisting of nerve growth factors NGF, BDNF, NT-3, NT-4, NT-6, anti-neurotrophin receptor antibodies MAb 5C3 and Mab MC192.

TABLE 2-continued

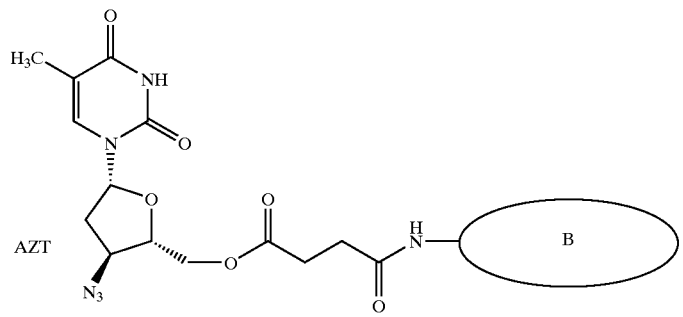

wherein B is selected from the group consisting of nerve growth factors NGF, BDNF, NT-3, NT-4, NT-6, anti-neurotrophin receptor antibodies MAb 5C3 and Mab MC192.

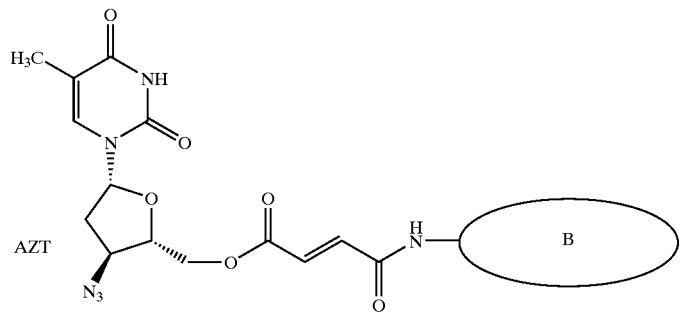

wherein B is selected from the group consisting of nerve growth factors NGF, BDNF, NT-3, NT-4, NT-6, anti-neurotrophin receptor antibodies MAb 5C3 and Mab MC192.

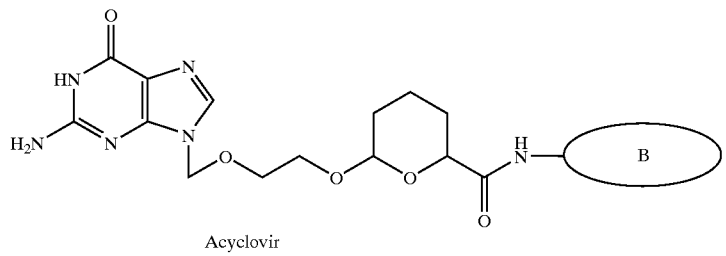

Acyclovir wherein B is selected from the group consisting of nerve growth factors NGF, BDNF, NT-3, NT-4, NT-6, anti-neurotrophin receptor antibodies MAb 5C3 and Mab MC192.

6. Methods for Using Compounds of the Present Invention

Described below are several methods for formulating and administering the compounds of the present invention. The compounds of the present invention may be employed in these and other applications.

a. Pharmaceutical Formulations Utilizing Compositions of the Present Invention The compounds of the present invention may be incorporated into a variety of pharmaceutical compositions including, but not limited to: a sterile injectable solution or suspension; hard or soft gelatin capsules; tablets; emulsions; aqueous suspensions, dispersions, and solutions; suppositories. Other pharmaceutically suitable formulations for delivering the compounds of the present invention to nerve cells may also be used and are intended to fall within the scope of the present invention.

b. Routes of Administration

The compounds according to the present invention can be administered orally, by subcutaneous or other injection, intravenously, intracerebrally, intramuscularly, parenternally, transdermally, nasally or rectally. The form in which the compound is administered depends at least in part on the route by which the compound is administered.

While the present invention is disclosed with reference to preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims. The patents, papers, and books cited in this application are to be incorporated herein in their entirety.

We claim:

1. A method for delivering a non-cytotoxic antiviral therapeutic moiety selectively into nerve cells, the method comprising:

administering a compound having the general formula:

B—L—TM where:
B is nerve growth factor (NGF) or a fragment thereof which selectively binds to a neurotrophin receptor;

TM is a noncytotoxic, antiviral therapeutic moiety other than a nerve growth factor or fragment thereof; and L is an enzymatically cleavable amide linker coupling B to TM, wherein binding of moiety B to a nerve cell neurotrophin receptor triggers absorption of the receptor-bound compound and delivery of the non-cytotoxic therapeutic moiety into the nerve cell.

2. The method of claim 1, wherein B is a synthetic of peptide of the NGF.

3. The method of claim 2, wherein B is un NGF fragment capable of binding to trkA and triggering absorption of the compound.

4. The method of claim 2, wherein B is an NGF fragment capable of binding to p75 and triggering absorption of the compound.

5. The method of claim 1, wherein TM is an antiviral selected from the group consisting of: acyclovir, gancyclovir, AZT, ddI, ddC, and cidofovir.

6. The method of claim 5, wherein said antiviral is acyclovir.

7. The method of claim 5, wherein said antiviral is gancyclovir.

8. The method of claim 5, wherein said antiviral is AZT.

9. The method of claim 5, wherein said antiviral is cidofovir.

10. A method for selectivity delivering an antiviral into nerve cells, the method comprising:

administering a compound having the general formula:

B—L—TM where;

B is a nerve growth factor (NGF) which selectively binds to a neurotrophin receptor;

TM is a noncytotoxic, antiviral therapeutic moiety selected from the group consisting of acyclovir, gancyclovir, AZT, ddI, ddC, and cidofovir; and L is an enzymatically cleavable amide linker coupling B to TM, wherein binding of moiety B to a nerve cell neurotrophin receptor triggers absorption of the receptor-bound compound and delivery of the antiviral into the nerve cell.

11. The method of claim 10, wherein B is capable of binding to trkA and triggering absorption of the compound.

12. The method of claim 10, wherein B is capable of binding to p75 and triggering absorption of the compound.

13. The method of claim 10, wherein said antiviral is acyclovir.

14. The method of claim 10, wherein said antiviral is gancyclovir.

15. The method of claim 10, wherein said antiviral is AZT.

16. The method of claim 10, wherein said antiviral is cidofovir.

* * * * *